United States Patent [19]

Weinstein

[11] Patent Number: 5,031,608
[45] Date of Patent: Jul. 16, 1991

[54] PROTECTIVE GUARD AID DEVICE DESIGNED FOR INJURED AND WOUNDED FINGERS AND/OR TOES

[76] Inventor: David J. Weinstein, 1109 Live Oak St., New Smyrna Beach, Fla. 32069

[21] Appl. No.: 57,439
[22] Filed: Jun. 3, 1987
[51] Int. Cl.$^5$ ............................................. A61F 05/04
[52] U.S. Cl. ................................. 128/87 A; 128/879; 128/880; 2/21
[58] Field of Search ................ 128/87 A, 81 A, 81 R, 128/153, 165, 133, 879, 880; 2/21

[56] References Cited

U.S. PATENT DOCUMENTS

| | | | |
|---|---|---|---|
| 772,197 | 10/1904 | Weaver | 2/21 |
| 1,273,256 | 7/1918 | Manning | 2/21 |
| 1,837,691 | 12/1931 | Thigpen | 128/87 A |
| 2,044,523 | 6/1936 | Bertram | 128/153 |
| 2,225,896 | 12/1940 | Belknap | 128/133 |
| 2,251,551 | 8/1941 | O'Reilly | 2/21 |
| 2,633,126 | 3/1953 | Newmark | 2/21 |
| 4,103,682 | 8/1978 | Franzl | 128/87 |
| 4,127,222 | 11/1978 | Adams | 2/21 |

Primary Examiner—Robert A. Hafer
Assistant Examiner—Kerry Owens

[57] ABSTRACT

This invention relates to an improved construction of finger and toe housing devices. It is adapted to be readily applied to the ends of fingers or toes for protecting injured and wounded areas.

Still another aim of the invention is to improve and provide a housing construction that may be economically manufactured and sold to be worn in order to protect and enable the wearer to perform their duties in the home and office, requiring the use of the hands and legs during the recovery period.

Still a further aim of the invention is to provide a strong protector of the class described of self-contained resilient molded bead-spine-hinged connected section having yieldable means of holding the sections in applied position with the built-in rear locking system 2 and 13, beyond the last joint of the finger or toe. Both sections 1 and 10 provide a convex apertured portion adapted to house the injured finger or toe during the recuperation period.

Still another aim of the device is to provide a strong, protective and completely encased storage holding area for the injured fingers or toes to heal safely and comfortably.

7 Claims, 1 Drawing Sheet

PROTECTIVE GUARD AID DEVICE DESIGNED FOR INJURED AND WOUNDED FINGERS AND/OR TOES

BACKGROUND OF THE INVENTION

1. Field of the Invention

The present invention relates generally to medical devices and more particularly to light weight molds adapted to immobilize digits (Injured and Wounded Fingers and/or Toes).

2. Description of the Related Art

Temporary immobilization of the fingers or toes is preferred or required to help prevent further tissue irritation and infection, and to reduce pain and swelling, which can be quite considerable. Such immobilization is ordinarily accomplished either by winding many turns of bandages tightly around the damaged area and the like to wholly enclose. In such instances, not only are the affected areas sealed in so that they tend to undesirably retain heat, but they are encased in unsightly, bulky coverings which interfere with normal movements of the body. Accordingly, there is a call for an attractive, simple, compact and light weight mold that will permit the free circulation of air and to exhaust heat from the affected areas by means of perforated holes throughout the entire mold.

SUMMARY OF THE INVENTION

The foregoing protective needs have been satisfied by the improved digit device of the present inventions. The device is self contained and simple, inexpensive, durable, attractive to view and easy to use and reuse, light in weight, comfortable and cool to wear, permitting the rapid dissipation of heat from the covered fingers and toes, and does not in any way interfere with normal use of unaffected digit areas.

The device is of a one piece solid molding which is bent in half, making a top and bottom housing, and to extend and encompass completely the full length of the finger or toe areas.

The device includes the improvement of a rear locking security connection system to prevent accidental opening, therefore to guarantee the protection for good healing; the molded device is also reasonably secured to the fingers or toes so as to provide an improved cosmetic appearance.

The invention housing is designed to enclose and completely store fingers and toes comfortably, more than the usual wrapping or bandaging, such as band-aids or small coverings in a most convenient manner. Another intent of manufacturing the device is to produce transparent devices and skin-tinted color plastic in order to blend as best as possible with the human body.

DESCRIPTION OF THE DRAWINGS

Referring more particularly to the accompanying drawings, which are for illustrative purposes only.

DESCRIPTION OF THE PREFERRED EMBODIMENT

Figure 1:
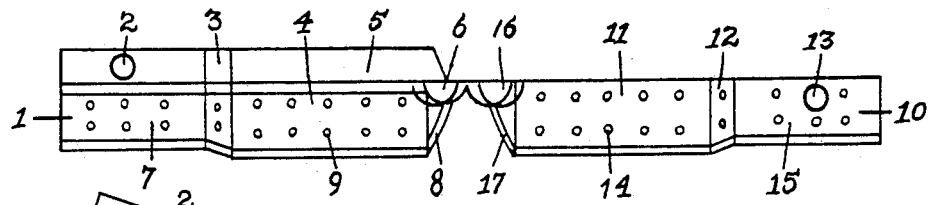
FIG. 1 is a pictorial view showing the present invention in the fully flattened and opened position before the insertion of the digit.

Referring more particularly to the drawings, wherein like reference characters designate like or corresponding parts throughout the different views:

FIG. 1. This device is shown in its fully opened and flattened position of the attached top section 1 to the bottom section 10. The protective overlapping top section 5, covers the complete length of the bottom section 11 on both sides when closed. The self-contained resilient molded bead-spine hinges 6 and 16 are located at the front center of the invention. The front top and bottom protective shields 8 and 17 are shown in their proper relationships as well. 1/16 inch holes 9 and 14 are placed throughout the complete device every ¼ inch apart in order to help body heat escape and air to circulate. The left top section 1 includes: rear top section 7, male snap lock 2, angular recess taper top section 3, expanded frontal section 4, full length overlapping area 5, 1/16 inch air circulation holes 9, self-contained resilient plastic molded spine-hinge 6. The right bottom section 10 includes: rear bottom section 15, female for male snap lock 13, angular recess taper bottom section 12, expanded frontal section 11, 1/16 inch air circulation holes 14, self-contained resilient plastic molded spine-hinge 16.

Figure 2:
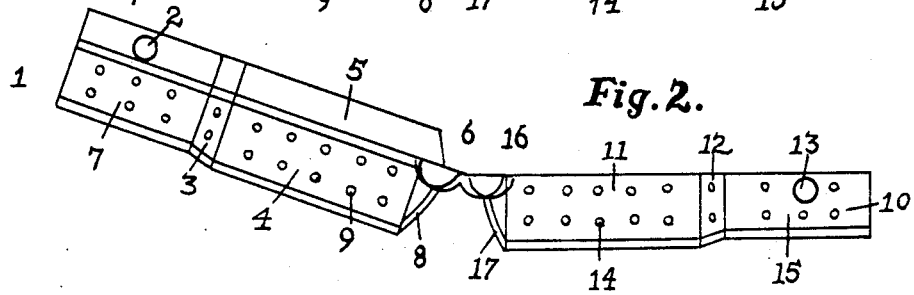
FIG. 2 is a pictorial view showing the invention in a semi-self-closing position.

FIG. 2. This view shows how the device starts to close onto one another 1 and 10, which is at its central axis 6 and 16. All corresponding identification numbers are repeated throughout the device as shown in FIG. 1. Numbers 1 through 18.

Figure 3:
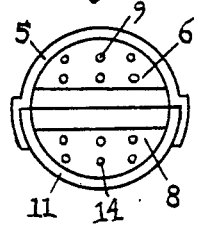
FIG. 3 is the front cut-away in the closed and overlapped position.

FIG. 3. Frontal top and bottom section cutaway in closed position 1 and 10. View shows the overlapping sections on both areas of device 5. It also shows the heat and air circulation 1/16 inch holes within the top and bottom sections 1 and 10. Also seen are the frontal self-contained resilient molded bead-spine-hinges 6 and 16.

Figure 4:
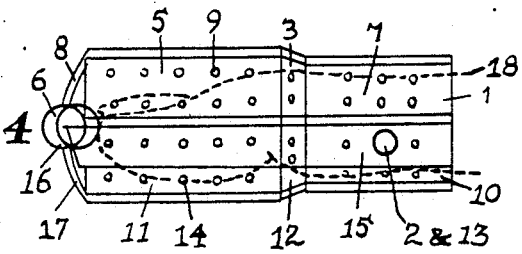
FIG. 4 is the fully closed (sideview) invention depicting the finger in the correct position which is fully surrounded and covered.

FIG. 4. The device is shown in its completely closed side view and locked rear position of the top and bottom sections 1 and 10, with an (art-dash-finger) to achieve a true housing relationship of the invention and the human body.

Figure 5:
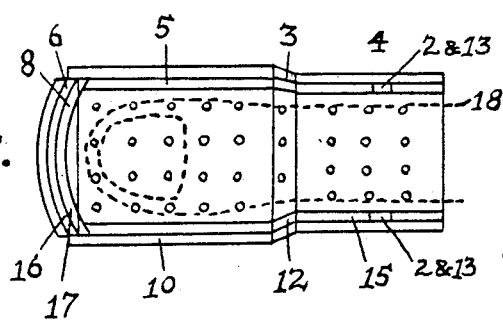
FIG. 5 is the fully closed (top view) invention depicting the finger in the correct position.

FIG. 5. Is the completely closed top view and locked rear position 1 and 10, with an (art-dash-finger) to achieve a true housing relationship of the invention and the human body.

Figure 6:
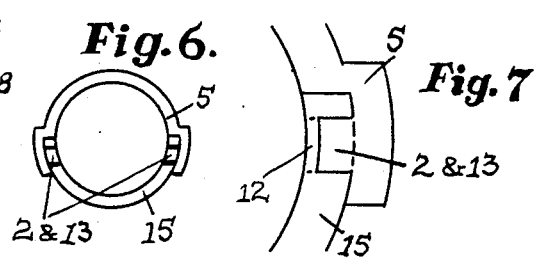
FIG. 6 is the back or rear cutaway view in the closed position depicting the two locking systems in unison.

FIG. 6. Rear top and bottom cutaway view in the completely closed side view 1 and 10. View shows top overlapping Section 5 onto bottom Section 10 and male and female snap locks in their correct closed position 2 and 13.

Figure 7:
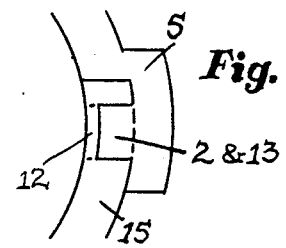
FIG. 7 is the detail view of the rear closed cutaway view depicting the locking system and showing the overlapping area.

FIG. 7. This view is a detailed cutaway of the closed and locked male and female positions of the top and bottom sections 1 and 10. It also shows the overlapping relationship 5.

Figure 8:
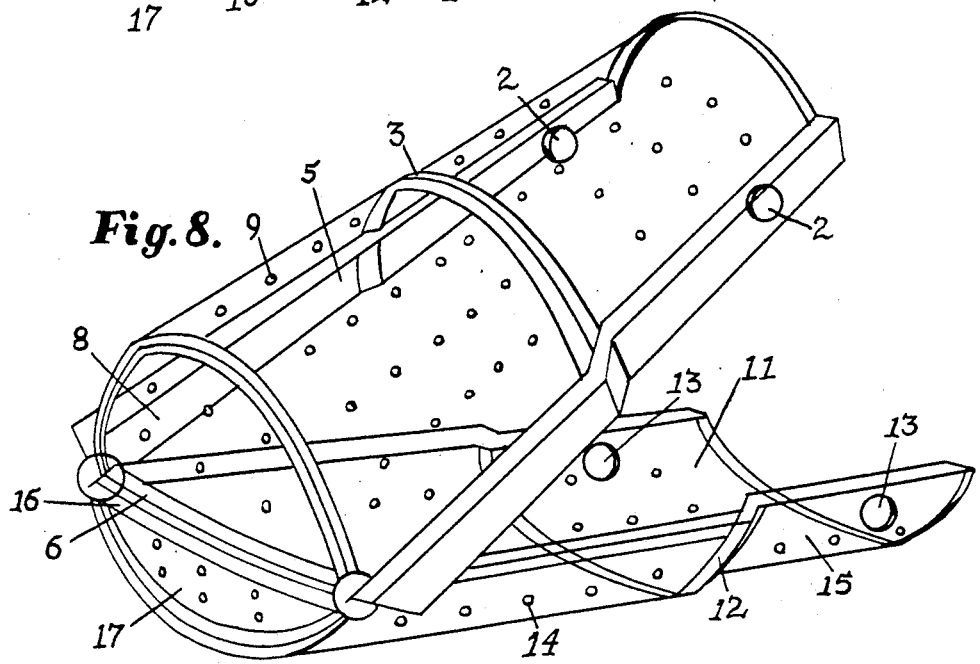
FIG. 8 is another arrangement of the present invention showing a three-quarter view in a partially closed position. Note the overlapping structure 5, on its way to seal and lock into its counterpart 10.

FIG. 8. This three-quarter view depicts the invention in a semi-closed down position which shows the overlapping top section 5, the self-contained resilient molded bead-spine-hinge 6 and 16, the male and female snap locks 2 and 13, and the 1/16 inch circulating holes 9 and 14.

I claim:

1. A protective guard for a digit comprising:
   a top housing having a convex configuration;
   a bottom housing have a concave configuration;
   said top and bottom housings having front and rear portions;
   an overlapping lip extending outwardly from both edges of said top housing, and spanning said top housing from said front portion to said rear portion;
   means for conecting said top and bottom housings at said front portion thereof;
   means for securely fastening said top and bottom housing to one another at said rear portions thereof;
   wherein said top and bottom housings, when connected and securely fastened, form a means for encircling a digit.

2. The protective guard of claim 1 wherein said means for connecting comprises a top frontal shield portion enclosing said front portion of said top housing, and a bottom frontal shield portion enclosing said front portion of said bottom housing;
   a first beaded spine hinge attached to said top frontal shield portion and a second beaded spine hinge attached to said bottom frontal shield portion, said first hinge being attached to said second hinge, thus joining said top and bottom housings.

3. The protective guard of claim 1 wherein said top and bottom housings comprise resilient, flexible, molded plastic with vent holes dispersed uniformly throughout.

4. The protective guard of claim 1 wherein said means for securely fastening comprises at least two inter-snap-locks, of which male portions are located at the rear portions of said overlapping lip.

5. The protective guard of claim 4 wherein said means for securely fastening comprises female portion of said inter-snap-locks located on said rear portion of said bottom housing.

6. The protective guard of claim 1 wherein said top and bottom housings comprise a frontal expansion portion area to accommodate additional space for the first and second joints of a digit.

7. The protective guard of claim 1 comprising a one-piece self contained molded plastic having three connected portions; (top housing, bottom housing and frontal shield); which incorporates an embodiment of: inter-snap-locks, overlapping-lips, beaded-spine-hinge, frontal expansion portion and vented holes.

* * * * *